(12) United States Patent
Stenzler et al.

(10) Patent No.: US 11,324,901 B2
(45) Date of Patent: May 10, 2022

(54) VAPOR INSERT FOR HOLDING A VAPOR SOURCE

(71) Applicant: PHILIP MORRIS PRODUCTS S.A., Neuchâtel (CH)

(72) Inventors: Alex Stenzler, Long Beach, CA (US); Steve Han, Huntington Beach, CA (US); James Tibbatts, Cambridge (GB); Steven Ellis, Oro-Medonte (CA)

(73) Assignee: Philip Morris Products S.A., Neuchatel (CH)

( * ) Notice: Subject to any disclaimer, the term of this patent is extended or adjusted under 35 U.S.C. 154(b) by 146 days.

(21) Appl. No.: 16/636,743

(22) PCT Filed: Aug. 8, 2018

(86) PCT No.: PCT/IB2018/055980
§ 371 (c)(1),
(2) Date: Feb. 5, 2020

(87) PCT Pub. No.: WO2019/030697
PCT Pub. Date: Feb. 14, 2019

(65) Prior Publication Data
US 2020/0214344 A1 Jul. 9, 2020

Related U.S. Application Data

(60) Provisional application No. 62/544,163, filed on Aug. 11, 2017.

(51) Int. Cl.
*A24F 40/485* (2020.01)
*A61M 15/06* (2006.01)
(Continued)

(52) U.S. Cl.
CPC .......... *A61M 15/06* (2013.01); *A24F 40/485* (2020.01); *A24F 42/20* (2020.01); *A24F 42/60* (2020.01); *A24F 40/20* (2020.01); *A24F 40/42* (2020.01)

(58) Field of Classification Search
CPC ....... A61M 15/06; A24F 40/485; A24F 40/42; A24F 40/40; A24F 42/20; A24F 42/60; A24F 40/20
(Continued)

(56) References Cited

U.S. PATENT DOCUMENTS 3,789,855 A * 2/1974 Norman ................. A24D 3/043
                                                           131/336
4,358,371 A    11/1982 Jameson et al.
(Continued)

FOREIGN PATENT DOCUMENTS

CN    206776745 U  * 12/2017  ............. A24F 40/51
CN    206776746 U  * 12/2017  ............. A24F 40/50
(Continued)

OTHER PUBLICATIONS

International Search Report and Written Opinion for PCT/IB2018/055980, issued by the European Patent Office, dated Nov. 30, 2018; 14 pgs.
(Continued)

*Primary Examiner* — Hae Moon Hyeon
(74) *Attorney, Agent, or Firm* — Mueting Raasch Group

(57) ABSTRACT

The present invention provides devices for holding one or more vapor sources in a media inhaler. The devices permit vapor from the one or more vapor sources to be introduced and entrained into a stream of inhaled media. The vapor insert device includes a hollow cylinder having a porous surface, an open anterior end, and an open posterior end. An anterior flange is attached to the open anterior end, and a
(Continued)

posterior flange is attached to the open posterior end. The anterior flange and the posterior flange each have a diameter that is larger than a diameter of the hollow cylinder to form a circumferential space around the hollow cylinder.

15 Claims, 3 Drawing Sheets

(51) Int. Cl.
*A24F 42/20* (2020.01)
*A24F 42/60* (2020.01)
*A24F 40/20* (2020.01)
*A24F 40/42* (2020.01)

(58) Field of Classification Search
USPC ................................................ 131/328, 329
See application file for complete search history.

(56) References Cited

U.S. PATENT DOCUMENTS

| | | | |
|---|---|---|---|
| 10,219,543 | B2 | 3/2019 | Gill et al. |
| 10,624,392 | B2 | 4/2020 | Batista et al. |
| 10,849,357 | B2 | 12/2020 | Roudier et al. |
| 2015/0053219 | A1 | 2/2015 | Roudier et al. |
| 2015/0313278 | A1 | 11/2015 | Brookbank et al. |
| 2017/0006917 | A1 | 1/2017 | Alvarez |
| 2017/0049153 | A1 | 2/2017 | Guo et al. |
| 2017/0156403 | A1 | 6/2017 | Gill et al. |
| 2017/0172211 | A1 | 6/2017 | Batista |
| 2018/0352860 | A1* | 12/2018 | Qiu ...................... H05B 1/0227 |

FOREIGN PATENT DOCUMENTS

| | | |
|---|---|---|
| CN | 2474747 Y | 1/2020 |
| GB | 2 313 311 A | 11/1997 |
| RU | 2607608 | 1/2017 |
| WO | WO 2016/168276 A1 | 10/2016 |
| WO | WO 2017/108394 A1 | 6/2017 |

OTHER PUBLICATIONS

International Preliminary Report on Patentability for PCT/IB2018/055980, issued by the European Patent Office, dated Nov. 14, 2019; 59 pgs.
Russian Office Action for RU 2020109329 issued by the Patent Office of the Russian Federation; dated Oct. 13, 2021: 15 pgs.
Chinese Office Action issued for CN 201880048375.1 by the Chinese Patent Office; dated Jul. 5, 2021; 13 pgs. including English Translation.
Chinese Office Action issued for CN 201880048375.1 by the Chinese Patent Office; dated Mar. 9, 2022; 12 pgs. including English Translation.

* cited by examiner

VAPOR INSERT FOR HOLDING A VAPOR SOURCE

This application is the § 371 U.S. National Stage of International Application No. PCT/IB32018/055980, filed 8 Aug. 2018, which claims the benefit of U.S. Application No. 62/544,163, filed 11 Aug. 2017, the disclosures of which are incorporated by reference herein in their entireties.

BACKGROUND OF THE INVENTION

There are a variety of devices on the market for inhaled media delivery, including gas inhalers, dry powder inhalers, and aerosol inhalers. The media inhaler devices can be utilized for medicament delivery and/or recreational use, but often do not provide the user with the ability to modify the inhalation experience outside of exchanging the inhaled media.

There is a need in the art for a means of enhancing inhaled media. The present invention addresses this need.

SUMMARY OF THE INVENTION

In one aspect, the invention relates to a vapor insert device comprising: a hollow cylinder having a porous surface, an open anterior end, and an open posterior end; an anterior flange attached to the open anterior end; and a posterior flange attached to the open posterior end; the anterior flange and the posterior flange each has a diameter that is larger than a diameter of the hollow cylinder to form a circumferential space around the hollow cylinder.

In one embodiment, the porous surface is constructed from a wire mesh. In one embodiment, the porous surface is constructed from a woven textile. In one embodiment, the porous surface is constructed from a solid material having one or more holes or slits.

In one embodiment, the device further comprises one or more struts extending from the anterior flange to the posterior flange. In one embodiment, the one or more struts partition the circumferential space by further extending from the surface of the hollow cylinder to the outer edge of the anterior flange and the posterior flange.

In one embodiment, the posterior flange comprises one or more apertures. In one embodiment, the anterior flange, the posterior flange, or both are at least partially constructed from a rubber or silicon material.

In one embodiment, the circumferential space fits one or more vapor sources. In one embodiment, the vapor source is selected from the group consisting of tobacco leaves, gel beads, flavoring agents, tea leaves, coffee grounds, and infused fibrous pads.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

DETAILED DESCRIPTION

The present invention provides devices for holding one or more vapor sources in a media inhaler. The devices permit vapor from the one or more vapor sources to be introduced and entrained into a stream of inhaled media.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Vapor Insert

The present invention provides vapor insert devices that are sized to fit within the airway of a media inhaler. The vapor inserts are capable of holding one or more vapor sources within the airway of the media inhaler. The vapor inserts permit vapor from the one or more vapor sources to enter the airway of the media inhaler, whereupon inhalation by a user entrains vapor into the media stream to simultaneously deliver media and vapor to the user.

Referring now to FIG. 1A and FIG. 1B, an exemplary vapor insert 10 is depicted. Vapor insert 10 comprises cylinder 12, anterior flange 14, and posterior flange 16. Cylinder 12 comprises a hollow interior and is open at both cylinder ends. Cylinder 12 comprises a surface 11 that permits the passage of air and vapor. In some embodiments, cylinder 12 comprises a mesh surface 11 that passes air and vapor, such as a woven textile or wire mesh material. In other embodiments, cylinder 12 comprises a solid surface 11 having one or more holes or slits that pass air and vapor. Cylinder 12 can have any suitable length, such as a length that fits within the airway of a media inhaler. Cylinder 12 can have any suitable width, preferably a width that is smaller than the airway of a media inhaler.

Figure 1B:
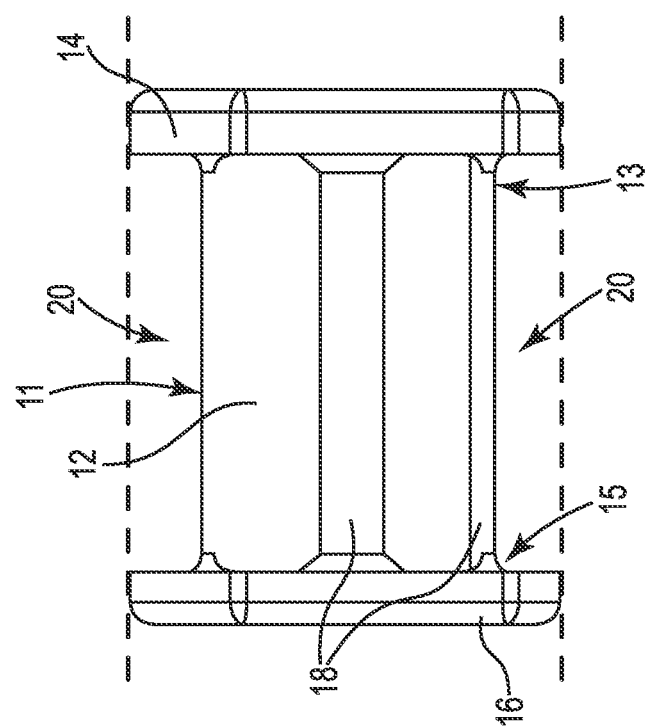
FIG. 1A and FIG. 1B depict perspective and side views of an exemplary vapor insert.
Figure 1A:
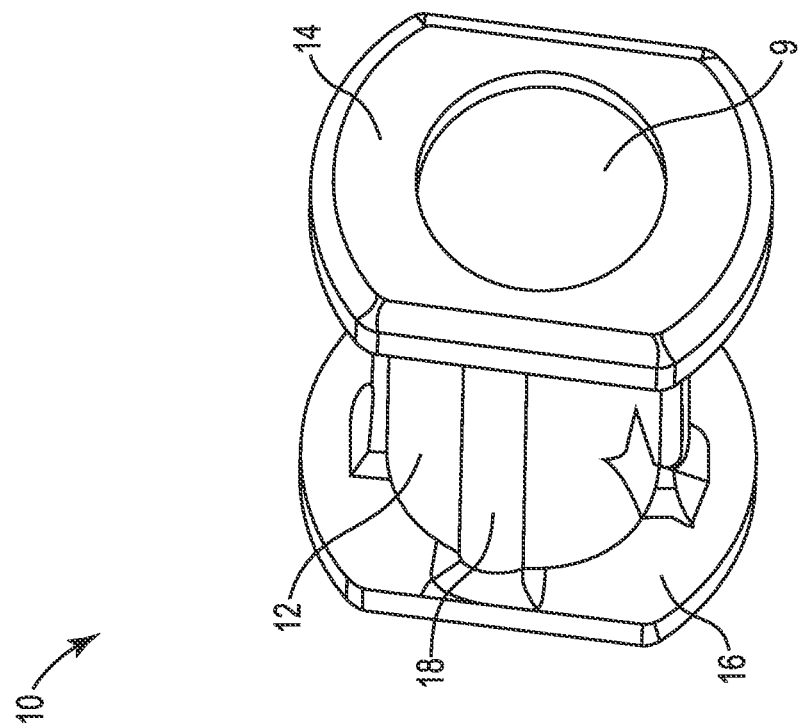
Figure 2B:
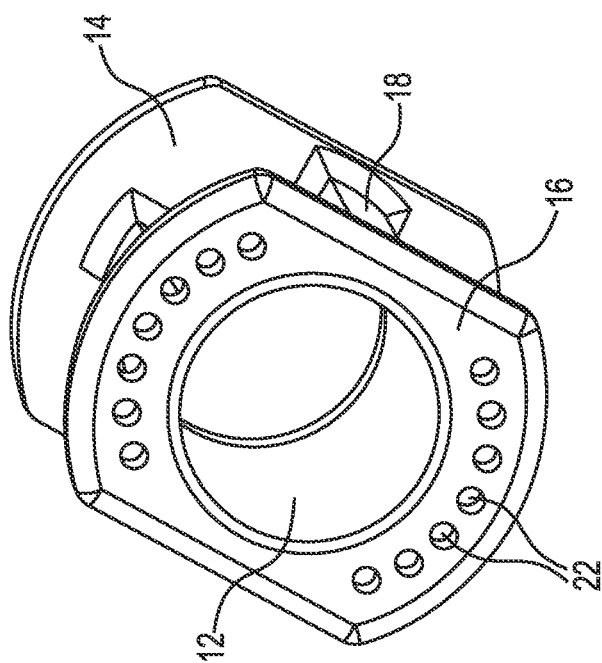
FIG. 2A and FIG. 2B depict perspective front and rear views of an exemplary vapor insert having apertures.
Figure 2A:
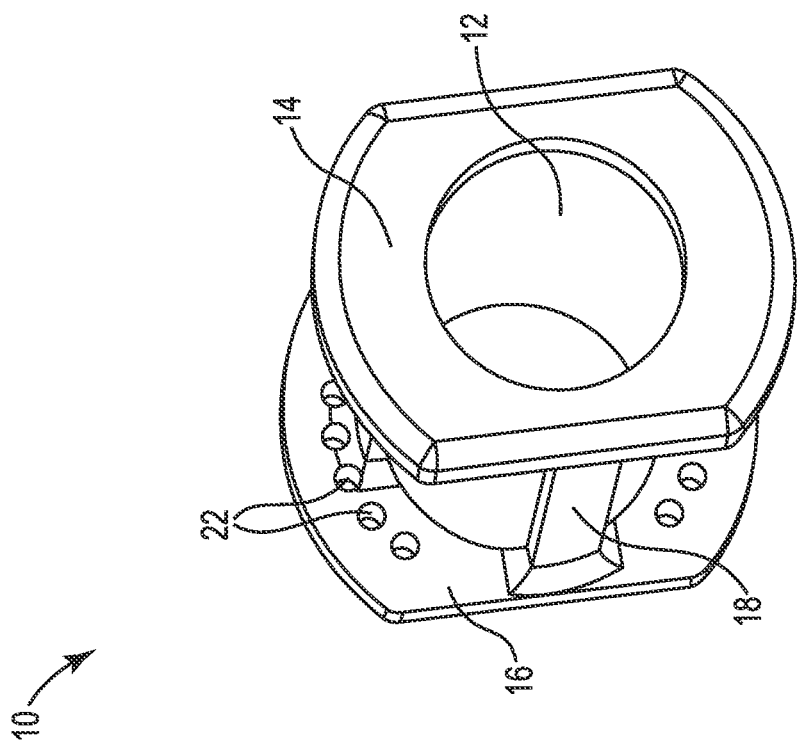
Figure 3A:
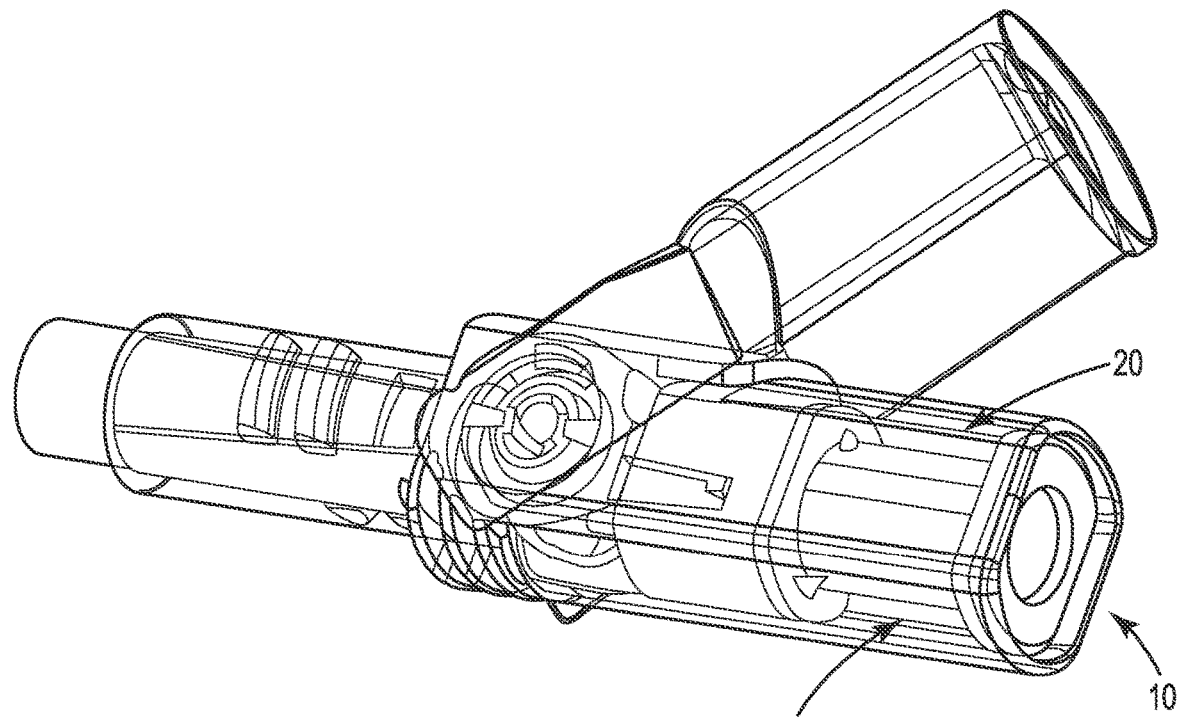
FIG. 3A and FIG. 3B depict an exemplary vapor insert placed within the airway of a media inhaler.
Figure 3B:
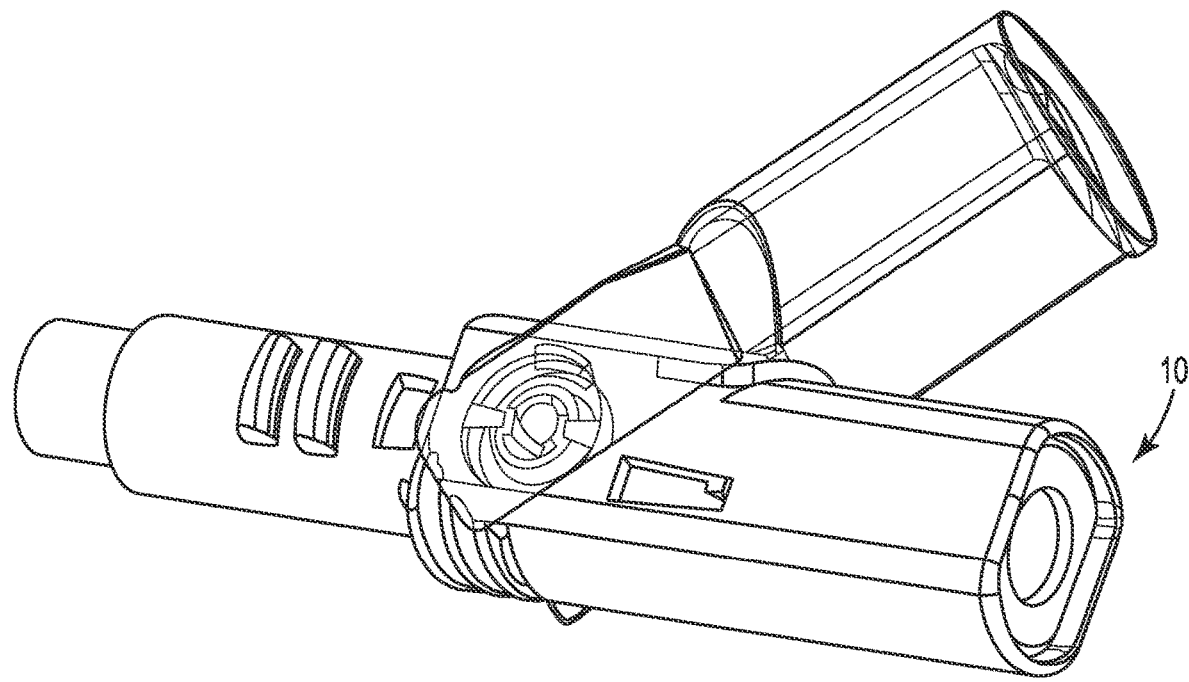

The anterior open end 13 of cylinder 12 is joined to anterior flange 14 and the posterior open end 15 of cylinder 12 is joined to posterior flange 16. Anterior flange 14 and posterior flange 16 are sized and shaped to fit flush within the airway of a media inhaler to securely position cylinder 12 within the airway. Referring now to FIG. 1B, vapor insert 10 is depicted with dashed lines to simulate the lumen of a media inhaler airway. Anterior flange 14 and posterior flange 16 have larger diameters than cylinder 12, and the diameter difference forms circumferential space 20 around cylinder 12. Anterior flange 14 and posterior flange 16 can be constructed from any suitable material, such as a metal or plastic. In certain embodiments, anterior flange 14, posterior flange 16, or both can be at least partially constructed from a rubber or silicone material to enhance fit and grip within the airway of a media inhaler. In certain embodiments, posterior flange 16 comprises one or more apertures 22 (FIG. 2A and FIG. 2B).

In certain embodiments, one or more struts 18 extend between anterior flange 14 and posterior flange 16. The one or more struts 18 are constructed from a stiff material, such as a metal or plastic, and enhance the structural stiffness of vapor insert 10, particularly if cylinder 12 is constructed from a flexible material. In certain embodiments, the one or more struts 18 can be sized to also extend from the outer surface of cylinder 12 and the outer edge of anterior flange 14 and posterior flange 16 (not pictured). In this manner, the one or more struts 18 partition circumferential space 20 into two or more compartments.

The various components of the present invention described above can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Referring now to FIG. 3A and FIG. 3B, an exemplary vapor insert 10 is depicted being inserted within the airway of a media inhaler. In the top image, the media inhaler is rendered semitransparent to depict circumferential space 20. In this manner, one or more vapor sources can be held within circumferential space 20. The one or more vapor sources can be any suitable aromatic material, such as gel beads, flavoring agents, tobacco leaves, tea leaves, coffee grounds, infused fibrous pads, and the like. As described elsewhere herein, cylinder 12 comprises a surface that permits the passage of air and vapor. When a user applies a vacuum to the media inhaler airway to draw in a dose of media, the flow of air passes through vapor insert 10. Air passing through vapor insert 10 may entrain vapor diffusing through cylinder 12 into its hollow interior. Air passing through vapor insert 10 may also pass through cylinder 12 to enter circumferential space 20 and entrain additional vapor. In certain embodiments, a vapor insert 10 having a posterior flange 16 with apertures 22 enhances the passing of air into circumferential space 20 to entrain additional vapor.

The invention further includes kits comprising one or more vapor inserts and one or more vapor sources. The one or more vapor sources can be provided as loose material or in small porous packets sized to fit within the circumferential space of the one or more vapor inserts for convenient insertion and removal.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A vapor insert device suitable for holding one or more vapor sources and sized to fit within the airway of a media inhaler, the vapor insert device comprising:

a hollow cylinder having a porous surface, an anterior open end, and a posterior open end, and the porous surface comprises a woven textile;

an anterior flange joined to the anterior open end; and a posterior flange joined to the posterior open end;

the anterior flange and the posterior flange each has a diameter that is larger than a diameter of the hollow cylinder to form a circumferential space around the hollow cylinder, wherein the circumferential space fits one or more vapor sources.

2. The device of claim 1, wherein the porous surface is constructed from a wire mesh.

3. The device of claim 1, further comprising one or more struts extending from the anterior flange to the posterior flange.

4. The device of claim 3, wherein the one or more struts partition the circumferential space by further extending from the surface of the hollow cylinder to the outer edge of the anterior flange and the posterior flange.

5. The device of claim 1, wherein the posterior flange comprises one or more apertures.

6. The device of claim 1, wherein the anterior flange, the posterior flange, or both are at least partially constructed from a rubber or silicon material.

7. The device of claim 1, wherein the vapor source is selected from the group consisting of tobacco leaves, gel beads, flavoring agents, tea leaves, coffee grounds, and infused fibrous pads.

8. A vapor insert device suitable for holding one or more vapor sources and sized to fit within the airway of a media inhaler, the vapor insert device comprising:

a hollow cylinder having a porous surface, an anterior open end, and a posterior open end;

an anterior flange joined to the anterior open end; and a posterior flange joined to the posterior open end;

the anterior flange and the posterior flange each has a diameter that is larger than a diameter of the hollow cylinder to form a circumferential space around the hollow cylinder, wherein the circumferential space fits one or more vapor sources.

9. The device of claim 8, wherein the porous surface is constructed from a wire mesh.

10. The device of claim 8, wherein the porous surface is constructed from a solid material having one or more holes or slits.

11. The device of claim 8, further comprising one or more struts extending from the anterior flange to the posterior flange.

12. The device of claim 11, wherein the one or more struts partition the circumferential space by further extending from the surface of the hollow cylinder to the outer edge of the anterior flange and the posterior flange.

13. The device of claim 8, wherein the posterior flange comprises one or more apertures.

14. The device of claim 8, wherein the anterior flange, the posterior flange, or both are at least partially constructed from a rubber or silicon material.

15. The device of claim 8, wherein the vapor source is selected from the group consisting of tobacco leaves, gel beads, flavoring agents, tea leaves, coffee grounds, and infused fibrous pads.

\* \* \* \* \*